United States Patent [19]

Fischer

[11] Patent Number: 4,875,376

[45] Date of Patent: Oct. 24, 1989

[54] GUIDED-BEND TEST APPARATUS

[76] Inventor: Glenn N. Fischer, Fischer Engineering Co., 7595 E. Singer Rd., Dayton, Ohio 45424

[21] Appl. No.: 205,980

[22] Filed: Jun. 13, 1988

[51] Int. Cl.$^4$ .............................................. G01N 3/20
[52] U.S. Cl. ........................................ 73/852; 73/850
[58] Field of Search .................................. 73/849–852

[56] References Cited

U.S. PATENT DOCUMENTS

| | | | |
|---|---|---|---|
| 2,277,204 | 3/1942 | Byier | 153/38 |
| 2,676,381 | 4/1954 | Holmes | 24/263 |
| 3,142,174 | 7/1964 | Baker | 73/100 |
| 3,500,679 | 3/1970 | Smith | 73/100 |
| 4,573,360 | 3/1986 | Yoneda | 73/850 |
| 4,625,563 | 12/1986 | Dawson et al. | 73/850 |
| 4,656,872 | 4/1987 | Fischer | 73/850 |
| 4,677,856 | 7/1987 | Fischer | 73/850 |

FOREIGN PATENT DOCUMENTS 920942 4/1954 Fed. Rep. of Germany .
805113 12/1979 U.S.S.R. .

Primary Examiner—Robert R. Raevis
Attorney, Agent, or Firm—Biebel, French & Nauman

[57] ABSTRACT

A self-contained apparatus for testing the ductility of a weld located within an elongated specimen having means for raising and lowering a ram over the specimen. The apparatus includes a pair of legs, each having a pair of spaced-apart rails for supporting a pair of spaced-apart rollers which define an opening. Each roller of a pair has a width sufficient for supporting the test specimen, and is connected to a corresponding rail pair to extend over the opening. An overarm is provided having a cylindrical bore for guiding a force-powering apparatus having a ram toward and away from the opening. A mandrel having a working surface is connected to the ram by an adapter. The mandrel is located with the working surface above but between the rollers. The specimen may be positioned on the rollers with the weld disposed between the rollers. The mandrel is forced downwardly by the ram, with the mandrel, contacting the specimen along the working surface to bend the specimen into the opening. The bending process exhibits the ductility of the weld as well as the presence of defects in the weld.

8 Claims, 8 Drawing Sheets

GUIDED-BEND TEST APPARATUS

BACKGROUND OF THE INVENTION

The present invention relates generally to an apparatus used in performing tests to determine the ductility of welds. Specifically, the test is carried out using the apparatus to operate upon a metallic weld test specimen by subjecting the specimen, in the vicinity of the weld, to a bending force.

It is frequently desirable or necessary to test the ductility of a weld joining two pieces of similar or dissimilar metallic materials. For example, as a product is being designed that will require welding for its assembly, the characteristics and performance of particular materials and welding techniques may be tested to ensure that they possess adequate ductility in compliance with applicable codes or standards. Failure to possess such ductility may result in a weld which can fracture when subjected to stresses or strains. As another example, training an individual in welding techniques or determining the individual's welding skill can be facilitated by testing the ductility of welds made.

The guided bend test has been widely used in the welding industry for the purposes noted above. A number of professional societies, such as the American Society of Mechanical Engineers, have defined standards for the uniform application of this test. In performing the test, a sample is made by welding two plates or two lengths of pipe together in end-to-end fashion. Single bar specimens are cut from the sample in such a way that the weld is either transverse or longitudinal to the length of the specimen. Each test specimen is supported at two points, with the weld positioned equidistantly between the support points. A ram having a curved working surface is moved into contact with the specimen at the weld, and is forced against the specimen, causing it to bend. The extent to which the specimen may be bent without breaking along the weld is indicative of the weld ductility. The presence of defects in the weld may also be exhibited by such a bend test.

A known test device for performing the guided bend test is shown in U.S. Pat. No. 3,500,679 issued Mar. 17, 1970 to Smith. The device includes a base having means for supporting the specimen at either end with the weld left unsupported. A hydraulic jack is mounted on the base, with a ram having a curved working surface being located for upward movement against the weld. A pair of rollers are positioned to be located above the specimen, so that the ram forces the specimen against the rollers in a manner that bends the specimen to drive it between the rollers.

The Smith device possesses several disadvantages. The lifting motion of the ram against the specimen from beneath the specimen causes difficulties in balancing the specimen such that bending force can be evenly applied.

A further problem experienced with apparatus such as the Smith device is slippage of the specimen about the ram periphery. This may occur if the thickness of the weld is different from that of the base metal or the weld metal is less ductile than the base metal. Slippage can also occur if the specimens are relatively thin.

What is needed, therefore, is an apparatus for use in bend testing which is portable and should include a means of support for the specimen, without slippage about the ram, and which will aid in alignment and centering of the weld with respect to the ram. Further, the apparatus must be capable of handling specimens of varying sizes. Moreover, despite relatively inexpensive construction, the apparatus must be sufficiently rugged to withstand the forces generated during performance of the test.

SUMMARY OF THE INVENTION

The present invention provides a self-contained apparatus for testing the ductility of a weld specimen taken from a sample formed by two plates or pipes connected in end-to-end fashion.

The apparatus includes first and second vertical pairs of legs each comprising a pair of horizontally aligned and spaced-apart rails. A pair of spaced-apart rollers defining an opening is provided, with each roller having a pair of ends and a width sufficient for supporting the specimen. Each roller is connected at its ends to a corresponding spaced-apart rail pair. An overarm having a cylindrical bore is provided for properly positioning a hydraulic cylinder for powering and guiding a ram for movement toward and away from the opening. A mandrel having a working surface is connected to the ram by an adapter. The mandrel is located, when the ram is in its raised position, with the working surface above but between the rollers. The specimen may be positioned upon the rollers with the weld disposed equidistant between the rollers. The mandrel is then forced downwardly by the ram to cause the mandrel to contact the specimen along the working surface, so as to bend the specimen into the opening.

Each of the rollers may be connected to a rail pair by means for releasably connecting the roller. Further, additional pairs of rollers having a variety of diameters may be provided, with the pairs of rollers being selectively interchangeable.

The apparatus may also include means for selectively moving the rollers toward and away from each other while supporting the rollers on the rails. This selective moving means can include a pair of L-shaped connecting brackets welded or otherwise attached between the rail pairs. The connecting brackets each include plate sections for slidably supporting a cylinder holder base. The connecting brackets further include plate sections having threaded bores for receiving threaded shafts. A pressure plate is positioned and attached to each end of the cylinder holder base. The pressure plate includes a smooth bore and threaded nut combination in axial alignment with the bore in the corresponding plate section. A handle is connected to the outer end of each threaded shaft for rotating the shaft thereby moving the rail pairs and the rollers inwardly or outwardly with respect to the centerline of the mandrel.

To prevent the legs from rotational movement due to the pressure exerted by the ram during operation, a foot is provided which connects one rail pair and includes a bore for receiving a threaded shaft. The threaded shaft having a threaded handle and nut combination on one end is connected at its other end by a pair of threaded nuts to a L-shaped bracket which connects the second rail pair. Rotation of the handle will cause the handle to tighten against the foot thereby reinforcing the legs against the force tending to rotate them.

The working surface may be a roughened surface. This roughened surface can be formed by knurling. Alternatively, the roughened surface can be defined by a plurality of pins embedded in the working surface.

Accordingly, it is an object of the present invention to provide a self-contained apparatus for use in performing the guided bend weld test; to provide such an apparatus for use in bend testing which is portable; to provide such an apparatus including means for supporting the specimen which will aid in alignment and centering of the weld with respect to the ram; to provide such an apparatus that is capable of use with various sizes of mandrels and test specimens without slippage around the mandrel; and to provide such an apparatus that is sufficiently rugged to withstand the forces generated during performance of the bend test.

Other objects and advantages of the present invention will be apparent from the following description, the accompanying drawings, and the appended claims.

DETAILED DESCRIPTION OF THE PREFERRED EMBODIMENT

Figure 1:
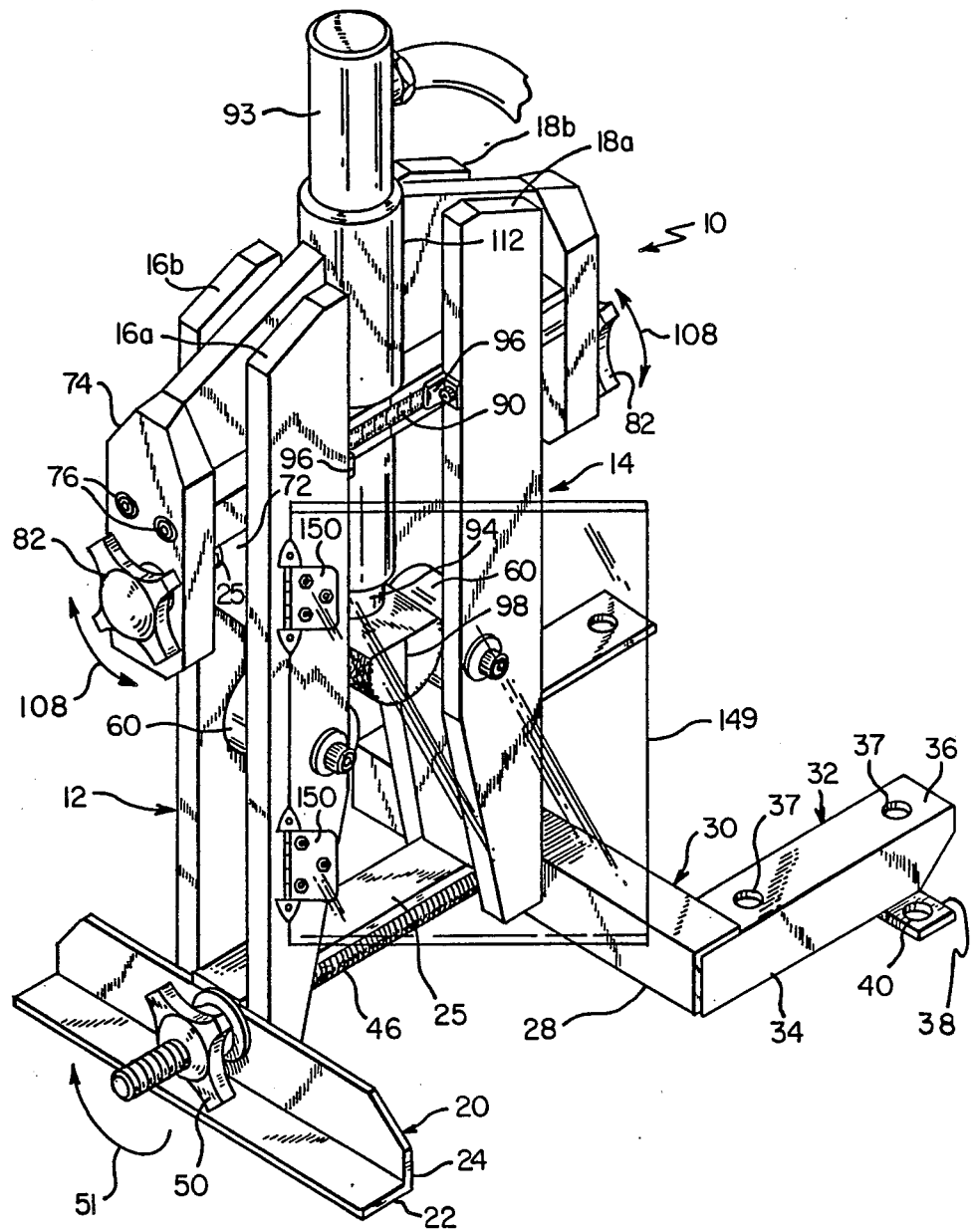
FIG. 1 is a front perspective view of a guided-bend test apparatus in accordance with the present invention.
Figure 2:
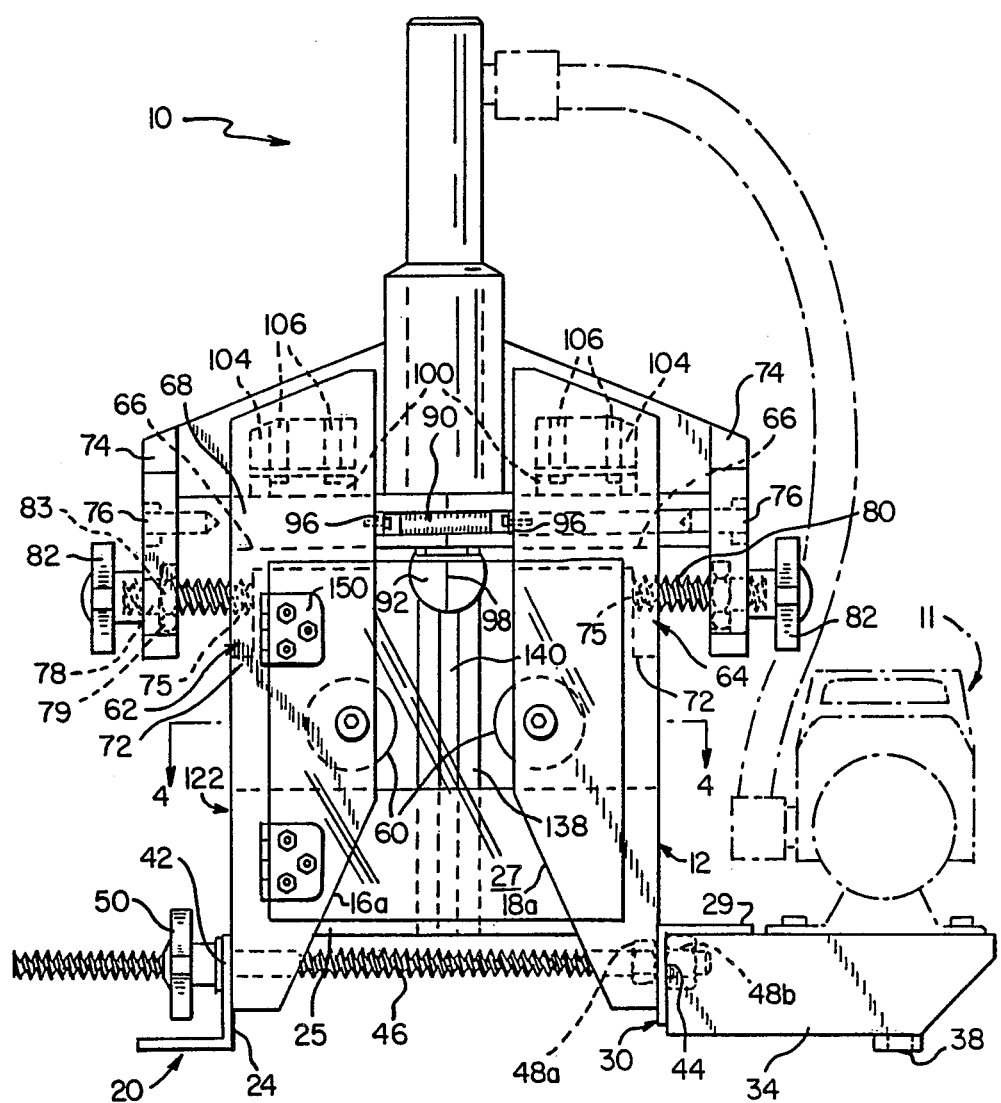
FIG. 2 is a front elevational view of the apparatus.

Referring generally to FIGS. 1 and 2, an apparatus 10 is shown having a force-powering apparatus 11 (shown in phantom in FIG. 2) for providing a ram that is capable of being raised and lowered away from and toward a bed. One such force-powering apparatus is a hydraulic cylinder and pump, manufactured by Enerpac of Butler, Wis.. However, other appropriate types of apparatus capable of generating sufficient downward force may also be used.

The apparatus 10 must be sufficiently rigid to withstand forces that are exerted upon it, as will be explained in detail below, by the force-powering apparatus. Thus, the various components of the apparatus 10 are formed from a rigid material, preferably a metallic material, and most preferably steel.

As seen in FIGS. 1 and 2, the apparatus 10 includes first and second vertical legs 12 and 14 each comprising a pair of vertically parallel and spaced-apart rails 16a and 16b, and 18a and 18b respectively. Rails 16a and 16b are connected at their lower ends by a foot 20 having a horizontal portion 22 and a vertical portion 24. Rails 18a and 18b are connected at their lower ends by a vertical portion 28 of a L-shaped bracket 30. A stand 32 is fixedly connected to the vertical portion 28 and the horizontal portion 29 of the L-shaped bracket 30. Vertically extending side plates 34 are mounted to the vertical and horizontal portions of the L-shaped bracket for supporting generally level, horizontal mounting flanges 36. Horizontal mounting flanges 36 having apertures 37, are adapted for supporting the force-powering apparatus 11 by bolts or other like means. Stand 32 further includes a pair of feet 38 mounted to each vertical side plate 34. Each foot 38 (see also FIG. 3) includes apertures 40 for mounting apparatus 10 to a support surface by bolts or other similar means.

Referring to FIG. 2, the vertical portion 24 of foot 20 and the vertical portion 28 of the L-shaped bracket 30, each include a hole 42 and 44 respectively, for receiving a threaded screw 46. The threaded screw 46 is secured to the vertical portion 28 using threaded nuts 48a and 48b and to the vertical portion 24 by a handle nut 50. A stop plate 25, extending in a direction parallel to the threaded screw 46 for supporting a cushion 27, is welded to the vertical portion 24 and the inside surfaces of rails 16a and 16b and as best seen in FIG. 1, is unattached at its opposite end.

Figure 4:
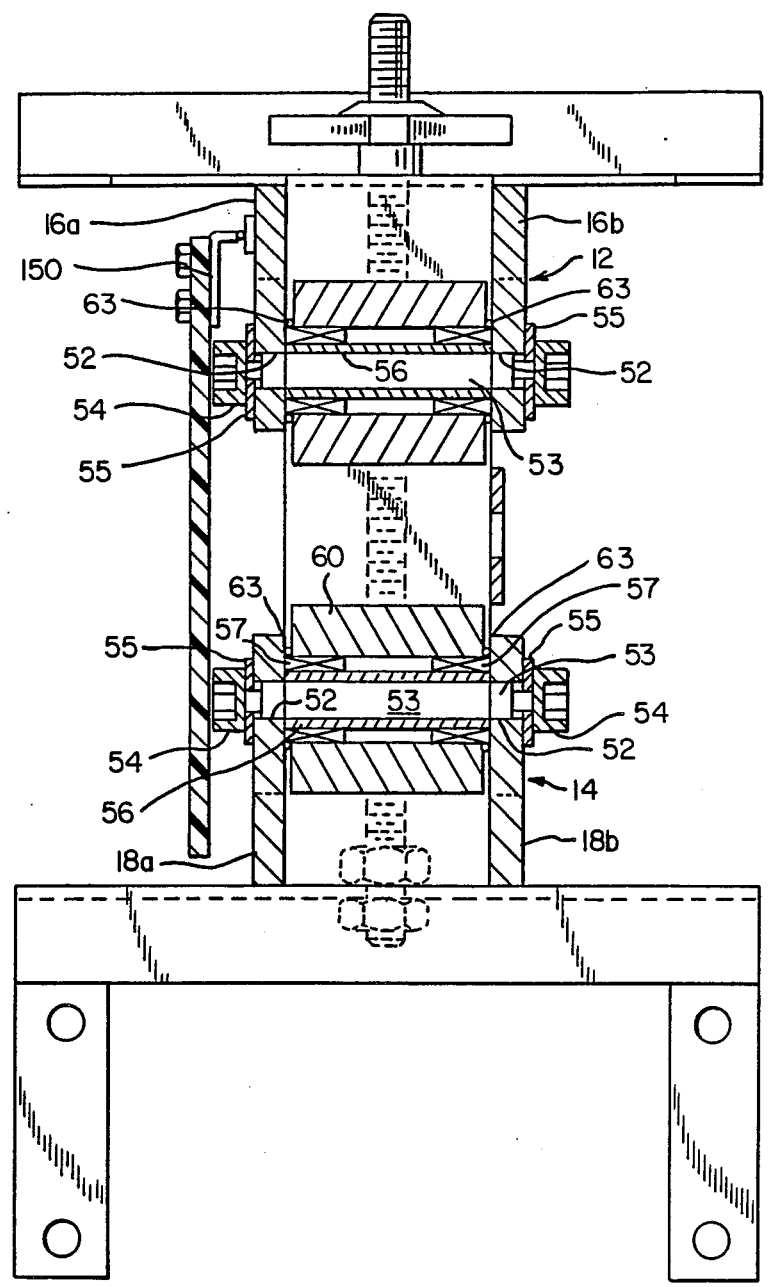
FIG. 4 is a top sectional view of the middle portion of the apparatus, taken generally along line 4—4 of FIG. 2.

As best seen in FIG. 4, each of the rails 16a, 16b, 18a and 18b are provided with a transverse bore 52. Bolts 53 are passed through each baces 52 of corresponding rails 16a and 16b, and rails 18a and 18b. O-rings 63 are provided at each end of the bearing assembly for preventing dust buildup on the bearing surfaces.

Roller shafts 53 are received in bores 52 and secured therein by cap screws 54 and washers 55. Shafts 53 receive cylindrical, sleeve-like spacers 56, which in turn receive pairs of bearings 57, which rotatably support rollers 60. Rollers 60 may be removed and relatively easily interchanged for different rollers, for reasons that will be explained in more detail below by simply removing cap screws 54 and washers 55.

Figure 3:
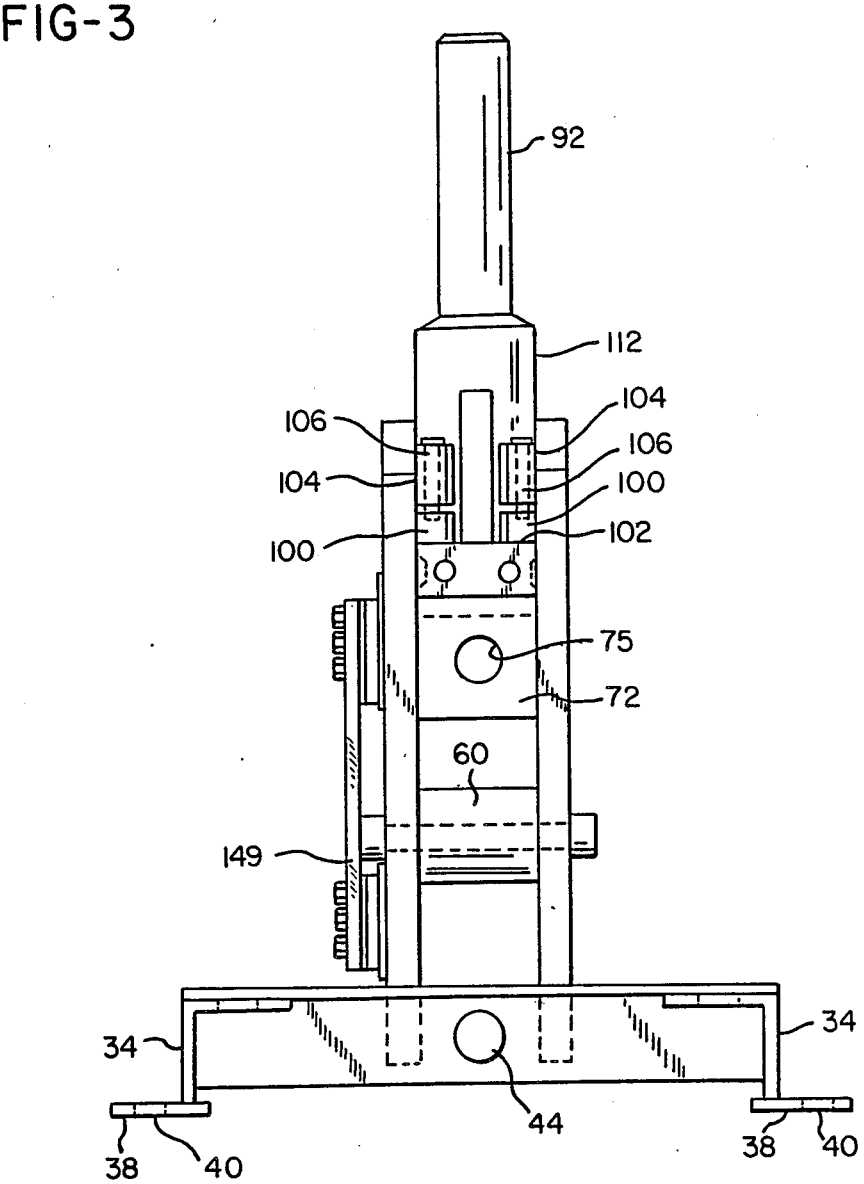
FIG. 3 is a right side view of the apparatus, the pressure plate and related components have been omitted.
Figure 9:
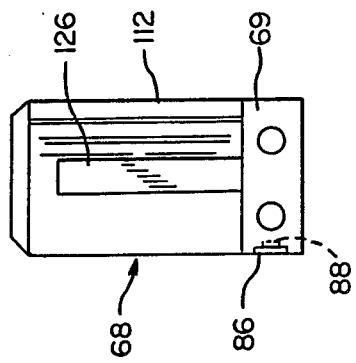
FIG. 9 is a side view thereof.
Figure 7:
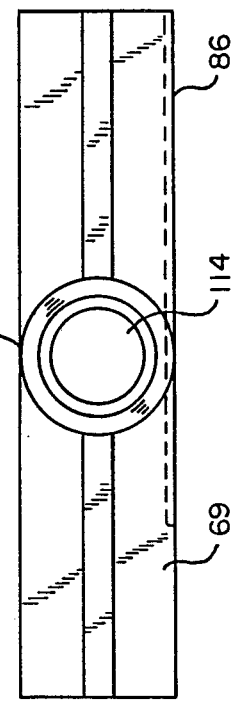
FIG. 7 is a top view of a cylinder holder base.

Referring to FIG. 2, a pair of L-shaped connecting brackets 62 and 64 are welded or otherwise attached between rails 16a and 16b, and 18a and 18b respectively (FIG. 1). The connecting brackets 62 and 64 each include horizontal plate sections 66 fixed to the rails in such a manner as to symmetrically extend horizontally in opposite sideward directions for slidably supporting a cylinder holder base 68, the latter also being shown in FIGS. 7 through 9. Connecting brackets 62 and 64 further include, as also seen in FIG. 3, vertical plate sections 72 connecting corresponding rails 16a and 16b, and 18a and 18b, and each includes a threaded bore 75 formed through the center of each vertical plate section 72 and in a direction parallel to the cylinder ram holder base 68.

As seen in FIGS. 1 and 2 pressure plate 74 is positioned and attached to each end of the cylinder ram holder base 68 by screws 76. The pressure plate 74 includes a smooth bore 78 and a an enlarged portion 79 formed through each plate 74 in axial alignment with the threaded bore 75, with bore 78 having a diameter slightly greater than that of a threaded shaft 80 (see FIG. 1).

Shaft 80 extends through smooth bore 78 and is threadably received in threaded bore 75. A handle 82 is fixed to the outer end of shaft 80, and a nut 83 is fixed to the shaft 80 where it passes through the enlarged portion 79.

Shown in FIGS. 1, 2, 7 and 8, the cylinder holder base 68 comprises a horizontally extending bar 69 having a generally rectangular cross section. The front face 84 of the bar 69 includes a slot 86 for mounting a scale 90 (not shown in FIGS. 7-9) which is used to accurately align rollers 60 with a centerline 98 inscribed on a side of the mandrel 92. As seen in FIGS. 1 and 2 scale indicators 96 are fixedly connected to rails 16a and 18a for positioning the rollers 60 relative to the centerline 98 of the mandrel 92.

As shown in FIGS. 2 and 3, legs 12 and 14 include horizontally extending gibs 100 which are in slidable contact with the upper surface 102 of the cylinder holder base 68. Horizontally extending flanges 104 are welded to rails 16 and 18 and include vertically extending gib take up screws 106 which contact gibs 100. By vertically extending or retracting screws 106, the operator can easily adjust gibs 100 to adjust for wear along the cylinder holder base 68. Furthermore, take up screws 106 can be adjusted to lock the cylinder holder base 68 in a desired position with respect to rollers 60.

Referring to FIGS. 1 and 2, to position rollers 60 for the proper mounting of a specimen relative to the centerline 98 of the mandrel 92, an operator of apparatus 10 may grip each handle 82 for rotation of shafts 80 in either direction, as indicated by arrows 108 (FIG. 1). This will result in horizontal movement of the legs 12 and 14 thereby moving rollers 60 either inwardly or outwardly with respect to the center line 98 of the mandrel 92.

To prevent for any misalignment of the rollers 60 as a result of movement of legs 12 and 14, due to pressure exerted by the ram 94 during operation, the operator may rotate handle nut 50, as indicated by arrow 51, to cause the handle to move inwardly along screw 46 and tighten against the foot 20 to reinforce legs 12 and 14. Of course, if the legs are to be moved outwardly from the position shown in FIGS. 1 and 2, handle 50 would first have to be threaded outwardly a distance sufficient to accommodate such outward movement, and then tightened as indicated above.

Figure 10:
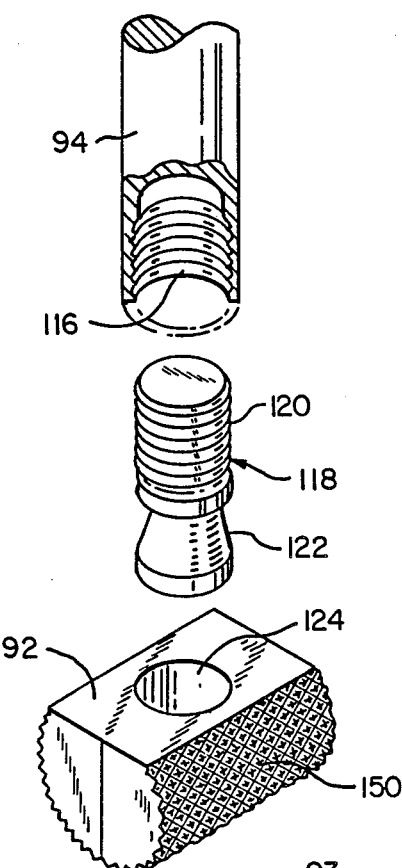
FIG. 10 is a perspective exploded view of the threaded adaptor, the end portion of the ram, and the mandrel.

As shown in FIGS. 1 and 7 through 9, the base 68 includes an elongated cylindrical center portion 112 having a cylindrical bore 114 formed there through for slidably receiving a hydraulic cylinder 93 having a ram 94. As shown in FIG. 10, the ram 94 includes a threaded end 116 for directly attaching to the mandrel 92 by a threaded adapter 118. The threaded adapter 118 comprises a threaded end 120 adapted for mating with the threaded end 116 of the ram 94, and a slide attachment beveled end 122 adapted to form a slip fit with a mating aperture 124 in the mandrel 92.

Figure 8:
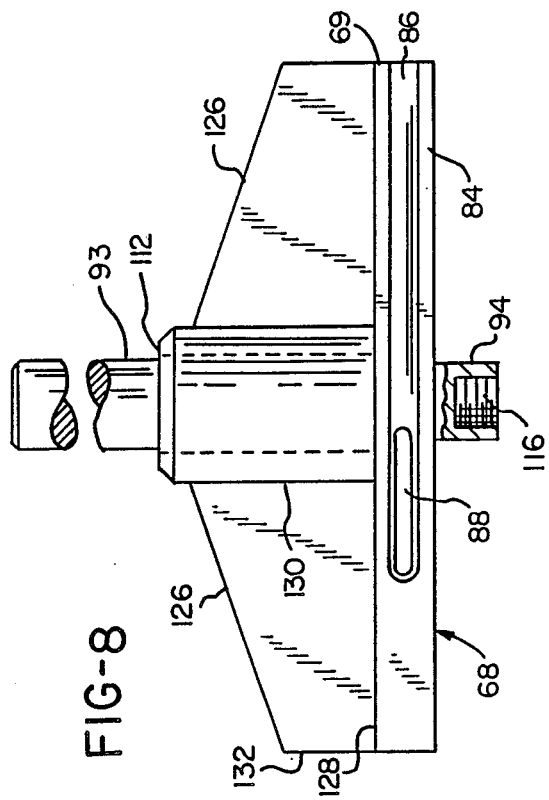
FIG. 8 is a front view of thereof.
Figure 6:
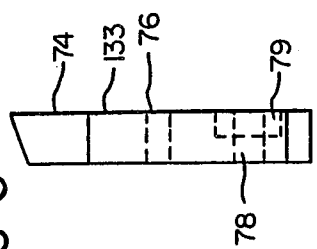
FIG. 6 is a side view of the pressure plate of FIG. 5.
Figure 5:
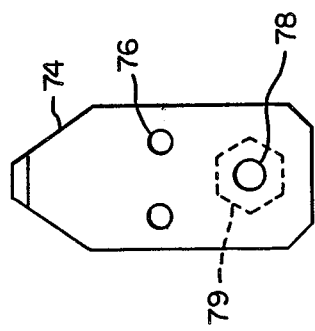
FIG. 5 is an end view of a pressure plate of the apparatus.

Referring to FIGS. 2 and 8, symmetrically extending in opposite sideward directions from the elongated cylindrical center portion 112 are gussets 126 each having a lower edge 128 securely fixed to the cylinder holder base 68 by welding or other similar means, and a vertical edge 130 securely fixed to the elongated cylindrical center portion 112, and a third edge 132 adapted to contact the back face 133 (see FIG. 6) of pressure plate 74.

Figure 12:
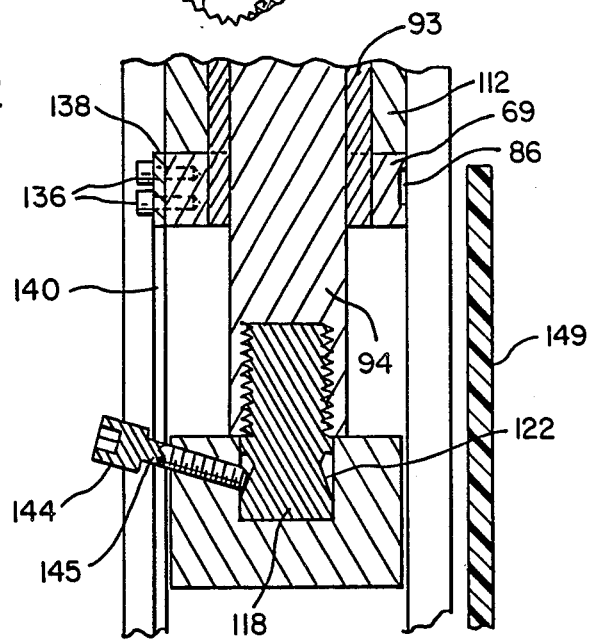
FIG. 12 is a detailed cross sectional side view taken along line 12—12 of FIG. 11.
Figure 11:
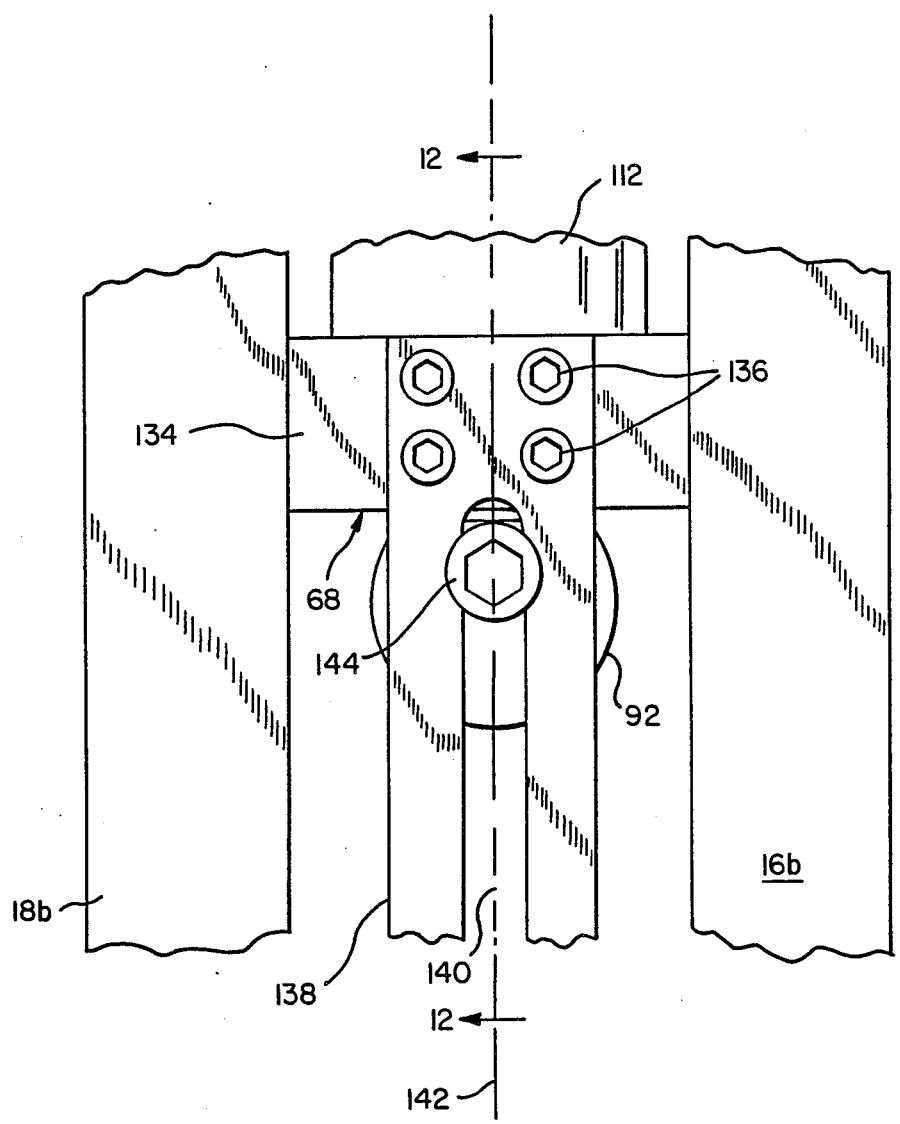
FIG. 11 is a back side sectional cutaway view of the apparatus.

Attached to the back side 134 (FIG. 11) of the cylinder holder 68 by screws 136 and extending vertically downwardly therefrom, is a mandrel guide plate 138. Guide plate 138 includes a longitudinally extending slot 140 having a centerline 142 parallel to the centerline 98 of the mandrel 92. As shown in FIGS. 10 and 12, mandrel 92 includes a slanted locking screw 144 which cooperates with the beveled end 122 of the adapter 118 for locking the mandrel 92 onto the adapter 118. The locking screw 144 includes a non threaded shoulder 145 adapted to slidably engage slot 140 of the guide plate 138 for maintaining the proper alignment of the mandrel 92 during extension or retraction of the ram 94.

Figure 13:
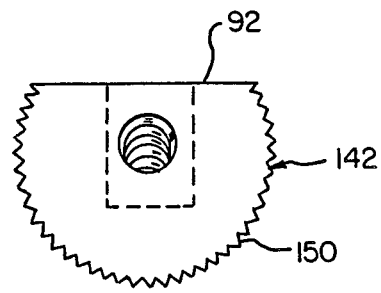
FIG. 13 is an end view of the mandrel working surface having a series of knurls.
Figure 14:
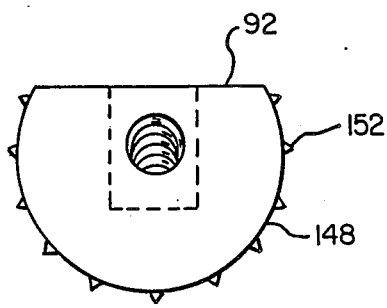
FIG. 14 is an end view of an alternative embodiment for the mandrel working surface having pointed pins.
Figure 15:
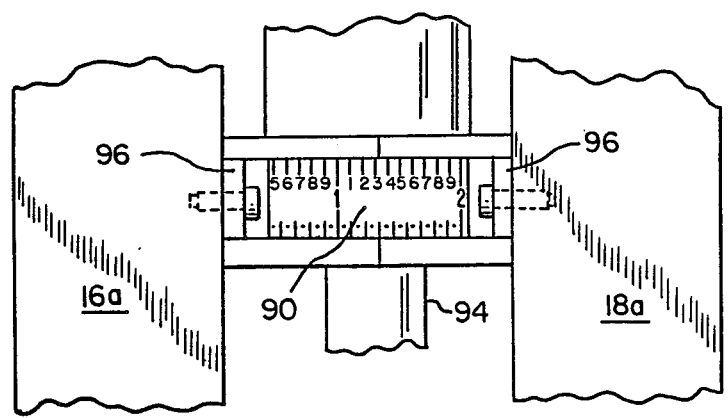
FIG. 15 is a detailed front elevational view of the scale.

Referring now to FIGS. 10 and 13, the mandrel 92 includes a curved, substantially cylindrical working surface 148. One common problem with weld testing apparatus has been a tendency of the specimen to slip with respect to the mandrel as bending force is being applied. Accordingly, surface 148 is provided with a series of knurls 150. An alternative to knurling this surface is shown in FIG. 14. Pointed pins 152 are embedded into the working surface 148 of mandrel 92. However, it should be recognized that still other alternatives for providing a roughened working surface 148 may be employed.

In one form of the invention (FIG. 1), the apparatus 10 is provided with a clear plastic, glass, or other similar material shield 149 hingedly mounted to rail 16a by hinges 150 to protect the operator from projected metal fragments in the event of specimen breakage.

The operation of the apparatus 10 will now be described with reference to FIG. 1. A specimen to be tested (not shown) is formed by welding two plates or two lengths of pipe together in end-to-end fashion in accordance with the techniques to be tested. Single bar specimens are cut from the sample in such a way that the weld is either transverse or longitudinal to the length of the specimen.

In accordance with industry standards, the radius dimensions of rollers 60 and of the circular working surface 148 of the mandrel 92, along with the relative spacing between rollers 60, are all determined by the dimensions and materials of the sample to be tested. Apparatus 10 therefore accommodates a variety of sizes of roller pairs 60 and working surfaces 148. The proper size of the mandrel is selected upon the basis of the specimen thickness and material.

Rollers 60 are installed by removing cap screws 54 and shafts 53 and placing the proper rollers on shafts 53 and locking them in place with cap screws 54. The mandrel 92 is most easily changed by removing the locking screw 144 (FIGS. 11 and 12) and pushing downwardly on the mandrel 92 to disengage the mandrel 92 from the adaptor 118. The appropriately sized mandrel 92 is then installed. Finally, the proper spacing between rollers 60 is achieved by manipulating handles 82 thereby moving rollers 60 either inwardly or outwardly. As noted above if the rollers are to be moved outwardly, it may be necessary to first rotate handle 50 counter clockwise as seen in FIG. 1, to space it outwardly away from the vertical portion 24, to provide room for vertical portion 24 to move outwardly along with the rails 16a and 16b to which it is attached and which carry the roller 60. After such outward movement, handle 50 is then threaded inwardly along shaft 46 to tighten handle 50 against vertical portion 24. By referring to scale 90, the proper spacing may be readily achieved. The handle nut 50 is then rotated until it snugly presses against the foot 20 to reinforce legs 12 and 14.

The apparatus 10 is provided with a force-providing apparatus which may be, for example, a pump having a hydraulically driven cylinder for driving a ram. The ram is attached to the mandrel using the appropriate mandrel adapter 118 (FIG. 10) and transmits a downward driving force to the mandrel 92, which in turn contacts the specimen. Further application of force drives the mandrel 92 against the specimen, causing it to bend downwardly between rollers 60. Force is continuously applied until the specimen is formed into a complete 180 degree bend and is ejected between legs 12 and 14, or until such time as the weld fractures, whereupon the specimen pieces will fall between legs 12 and 14. The cushion 27 provides padding to absorb impact of mandrel 92. The amount of force applied, or the extent to which the specimen is bent, or both, may be noted and the force exerted upon the mandrel 92 is released.

As force is reduced, the ram 94 is raised and the mandrel 92 is thereby raised to its original position, whereupon the apparatus 10 is ready for a next succeeding test.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. Guided-bend test apparatus comprising:
   opposed pairs of spaced, vertically extending legs,
   roller means supported intermediate upper and lower ends of said pairs of vertically extending legs,
   bracket means fixed to each of said pairs of legs above said roller means and adjacent upper ends of said legs and including substantially horizontally disposed portions,
   cylinder ram holder base means bridging said opposed pairs of vertically extending legs and supported by and slidably engaging said horizontally disposed portions of said bracket means, and
   means interconnecting said cylinder ram holder base means and said bracket means for effecting relative sliding movement therebetween, whereby the apparatus is used to carry out a guided-bend test.

2. The apparatus of claim 1 further comprising stabilizing means interconnecting said opposed pairs of spaced, vertically extending legs intermediate lower ends thereof.

3. The apparatus of claim 2 wherein said stabilizing means comprises:
   a screw threaded rod extending between said opposed pairs of spaced, vertically extending legs beneath said rollers and adjacent said lower ends of said legs, said screw threaded rod being fixed adjacent one end thereof to one of said pairs of legs, a vertically extending member secured to the other of said opposed pairs of vertically extending legs and having a smooth bore opening therethrough, and
   a handle complementarily threaded with respect to and received on said screw threaded rod outwardly of said vertically extending legs;
   whereby, after relative sliding movement is effected between said cylinder ram holder base means and said bracket means said threaded handle may be tightened against said vertical surface for stabilization of said apparatus.

4. The apparatus of claim 1 further comprising:
   mandrel means mounted on said cylinder ram holder base means for vertical movement with respect thereto, and
   guide means extending vertically intermediate said opposed pairs of legs and engaging said ram means for maintaining proper alignment thereof during vertical movement thereof.

5. The apparatus of claim 1 wherein said cylinder ram holder base means includes horizontally extending bar means having upper and lower sufaces,
   said lower surface thereof is in engagement with said horizontally disposed portions of said bracket means, and
   further comprising means slidably engaging said upper surface of said bar means.

6. The apparatus of claim 5 wherein said means engaging said upper surfaces of said bar means includes means for locking said cylinder ram holder base means with respect to said rollers.

7. The apparatus of claim 1 wherein said bracket means further includes vertically extending portions received between spaced legs of each of said pairs thereof, and
   said means interconnecting said cylinder ram holder base means and said bracket means for effecting relative sliding movement therebetween includes a threaded rod and a complementarily threaded aperture formed in said vertically extending portion of said bracket means.

8. Guided-bend test apparatus comprising two pairs of plate-like, vertically extending spaced apart legs,
   a foot having horizontally and vertically extending portions secured to lower ends of one of said pairs of legs,
   a L-shaped bracket having horizontally and vertically extending portions secured to the lower ends of the other of said pair of legs,
   said vertically extending portions of said foot and said bracket each having aligned openings therethrough,
   a threaded screw extending through said openings and fixed against movement longitudinally thereof with respect to said bracket,
   a handle complementarily threaded and received on said screw outwardly of said vertically extending portions of said foot and adapted to be threaded into engagement therewith,
   shafts extending between legs of each of said pairs of legs intermediate upper and lower ends thereof and each supporting a roller between each of said legs of said pairs of legs,
   substantially L-shaped second and third brackets received between and fixed with respect to said legs of each of said pairs of legs and having substantially horizontally and vertically disposed surfaces,
   means defining a screw threaded opening through said vertical surfaces of said second and third brackets,
   a cylinder ram holder base having a horizontally extending bar portion slidably engaging said horizontal surfaces of said second and third brackets,
   a pressure plate fixed to opposite ends of said cylinder ram holder base means outwardly of said vertically extending legs and having a smooth bored opening therethrough in line with said threaded openings in said vertically extending portions of said second and third brackets,
   a screw thread extending through each of said smooth bored openings in said pressure plates and threadably received in said threaded openings in said vertically extending portions of said second and third brackets,
   said screw threads being fixed against movement longitudinally thereof with respect to said pressure plates and having handle means fixed to an outer end of each outwardly of said pressure plates, means mounted on inner opposed surfaces of each of said legs of each of said pairs of legs and slidably engaging upper surfaces of said cylinder ram holder base, means for locking said means engaging said upper surface of said cylinder ram holder base to said upper surfaces thereof, an elongated cylindrical center portion on said cylinder ram holder base disposed medially thereof and having a cylindrical bore formed therethrough for slidably receiving a hydraulic cylinder having a ram mounting a mandrel to a lower end thereof, and means defining a vertically extending guide slot fixed to said cylinder ram holder base and depending downwardly therefrom intermediate said opposed pairs of spaced, vertically extending legs and receiving a portion of said mandrel for guidance thereof during vertical movement thereof toward and away from said rollers, whereby the apparatus is used to carry out a guided-bend test.

* * * * *